United States Patent
Day

(10) Patent No.: US 7,995,094 B2
(45) Date of Patent: Aug. 9, 2011

(54) GLAZING INSPECTION

(75) Inventor: Stephen Roland Day, Greater Manchester (GB)

(73) Assignee: Pilkington PLC, St. Helens, Merseyside (GB)

( * ) Notice: Subject to any disclaimer, the term of this patent is extended or adjusted under 35 U.S.C. 154(b) by 1684 days.

(21) Appl. No.: 11/178,361

(22) Filed: Jul. 12, 2005

(65) Prior Publication Data

US 2006/0013510 A1 Jan. 19, 2006

(30) Foreign Application Priority Data

Jul. 16, 2004 (GB) .................................. 0415916.6

(51) Int. Cl.
*H04N 7/18* (2006.01)
(52) U.S. Cl. ........................ 348/131; 348/125
(58) Field of Classification Search ........... 348/125–134
See application file for complete search history.

(56) References Cited

U.S. PATENT DOCUMENTS

| H503 H | * | 8/1988 | Keller ...................... 356/139.03 |
|---|---|---|---|
| 5,319,214 A | * | 6/1994 | Gregory et al. ............ 250/504 R |
| 5,446,536 A | | 8/1995 | Miyake et al. |
| 5,589,852 A | | 12/1996 | Thompson et al. |
| 5,986,640 A | | 11/1999 | Baldwin et al. |
| 6,100,990 A | * | 8/2000 | Ladewski ...................... 356/445 |
| 6,671,005 B1 | | 12/2003 | Pujol et al. |
| 2004/0239901 A1 | | 12/2004 | Wasserman et al. |

FOREIGN PATENT DOCUMENTS

| EP | 0 484 237 A1 | 5/1992 |
|---|---|---|
| EP | 1 061 357 A2 | 12/2000 |
| GB | 2 152 210 A | 7/1985 |
| WO | 99/34301 A1 | 7/1999 |

OTHER PUBLICATIONS

Giovanna Sansoni et al., "A Novel, Adaptive System for 3-D Optical Profilometry Using A Liquid Crystal Light Projector", IEEE Transactions on Instrumentation and Measurement, Aug. 1, 1994, pp. 558-565, vol. 43, No. 4, XP-000466818, IEEE Inc., New York, U.S.
Combined European Search Report and Written Opinion dated Nov. 25, 2005.
Summons to Attend Oral Proceedings Pursuant to Rule 115(1) EPC issued in corresponding EP Application No. 05 254 262.8, Mar. 14, 2008, EPO, Munich DE.
Huang, Peisen S., et al., "High-speed 3-D shape measurement based on digital fringe projection," *Opt. Eng.*, Jan. 2003, pp. 163-168, vol. 42, No. 1, Society of Photo-Optical Instrumentation Engineers, Bellingham, WA, US.
Communication Pursuant to Article 96(2) EPC (in English), issued by the European Patent Office in corresponding European Patent Application No. 05 254 262.8, Jun. 4, 2007.

* cited by examiner

*Primary Examiner* — David Czekaj
(74) *Attorney, Agent, or Firm* — Buchanan Ingersoll & Rooney PC

(57) ABSTRACT

A method and apparatus for inspection of the optical quality of a glazing is provided. A greyscale image is generated digitally, and reflected off or transmitted through a glazing, and captured using an image capture device. Preferably, the generation of the greyscale pattern and the capturing of the reflected or transmitted greyscale pattern are synchronised.

9 Claims, 2 Drawing Sheets

GLAZING INSPECTION

FIELD OF THE INVENTION

This invention relates to glazing inspection, in particular to a method and apparatus for determining the optical quality of a glazing in reflection or transmission, in particular a vehicle glazing, in which a greyscale pattern is either reflected off the product or transmitted through it and captured, and then subsequently processed.

DESCRIPTION OF THE PRIOR ART

In the production of vehicle glazings it is desirable to inspect every glazing to determine its optical quality, to ensure that it is acceptable for use as a vehicle glazing. One such inspection technique involves a method of capturing an image of a greyscale pattern reflected off a vehicle glazing and subsequently processing the image, is disclosed in EP1061357.

Greyscale patterns are commonly generated by transmitting light through LCDs (liquid crystal displays) but this is problematic due to the sensitivity of LCDs to temperature. As the temperature decreases the LCD fluid requires a higher operating voltage to maintain a given optical contrast. Thus at a constant operating voltage the optical contrast varies with changes in temperature, which can lead to unreliable patterns being produced. In addition, LCDs have a relatively low image brightness and contrast and so the quality of the pattern reflected from the glazing is poor and may cause difficulties in obtaining reliable results.

It is an object of the invention to improve the quality of greyscale patterns produced in glazing inspection techniques.

SUMMARY OF THE INVENTION

According to an aspect of the invention there is provided a glazing inspection apparatus for determining the optical quality of a glazing in which a greyscale pattern is generated and reflected off or transmitted through the glazing and captured by an image capture device for subsequent processing, wherein the greyscale pattern is generated by digital means.

In a preferred embodiment the digital means comprises a digital video projector which preferably includes a digital micromirror device (DMD). Such a device is less sensitive to temperature than LCDs and has good image brightness and contrast, and therefore produces more reliable greyscale patterns.

Preferably, the image capture device has an exposure time determined by the period of a pulse width modulation signal of the digital greyscale pattern generator. Preferably synchronising means are provided to synchronise the image capture device and the digital greyscale pattern generator.

The image capture device is preferably a CCD camera.

In a preferred embodiment the CCD camera has an exposure time which is set to be identical to the pulse width modulation of the digital video projector.

Preferably, the CCD camera has an exposure time which is set to be identical to a pulse width modulation period of the digital video projector.

Preferably, the CCD camera has an exposure time which is set to be equal to an integer multiple of a pulse width modulation period of the digital video projector.

Preferably, the exposure time of the CCD camera is synchronised with the pulse width modulation period of the digital video projector. Such an apparatus facilitates a high speed system.

The glazing being inspected may be an automotive glazing.

According to a further aspect of the invention there is provided a glazing inspection method for determining the optical quality of a glazing comprising the steps of: generating a greyscale pattern; reflecting the greyscale pattern off the glazing or transmitting it through the glazing; capturing the reflected or transmitted greyscale pattern for subsequent processing; wherein the greyscale pattern is digitally generated.

Preferably the generation of the greyscale pattern and capturing of the reflected or transmitted greyscale pattern are synchronised.

Preferably, the period of pulse width modulation signal used in generating the greyscale pattern is used to determine an exposure time used in capturing the reflected or transmitted greyscale pattern.

The method may be used to inspect automotive glazings.

BRIEF DESCRIPTION OF THE DRAWINGS

Embodiments of the invention will now be described with reference to the accompanying drawings in which.

DETAILED DESCRIPTION OF THE PREFERRED EMBODIMENTS

Figure 1:
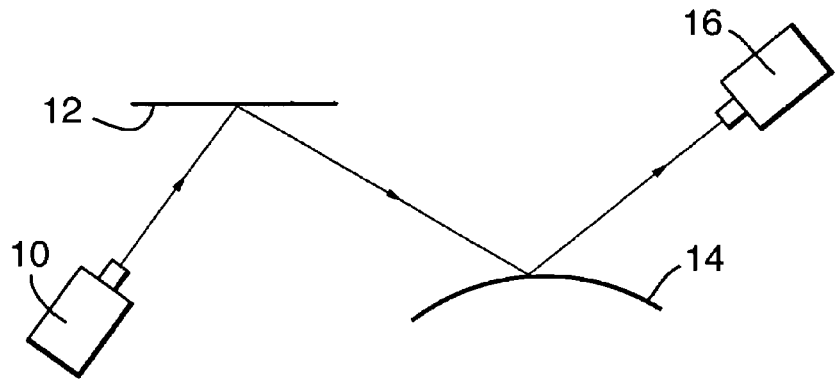
FIGS. 1 to 4 are schematic views of an arrangement of apparatus according to different embodiments of the invention.
Figure 2:
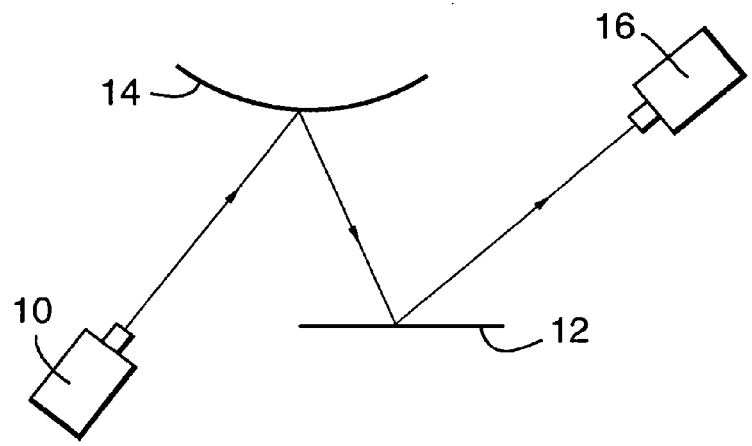

FIGS. 1 and 2 illustrate an arrangement of apparatus according to an embodiment of the invention for determining the optical quality of a glazing in reflection. In FIG. 1 a digital video projector 10 projects a sinusoidal greyscale pattern onto screen 12. A CCD camera 16 captures images of the greyscale pattern as reflected off glazing 14, which is shown as being curved but may be flat. FIG. 2 illustrates an alternative arrangement where the digital video projector 10 projects a sinusoidal greyscale pattern directly onto the glazing 14 which reflects it onto screen 12 and CCD camera 16 captures images of the reflected greyscale pattern from the screen 12.

Figure 3:
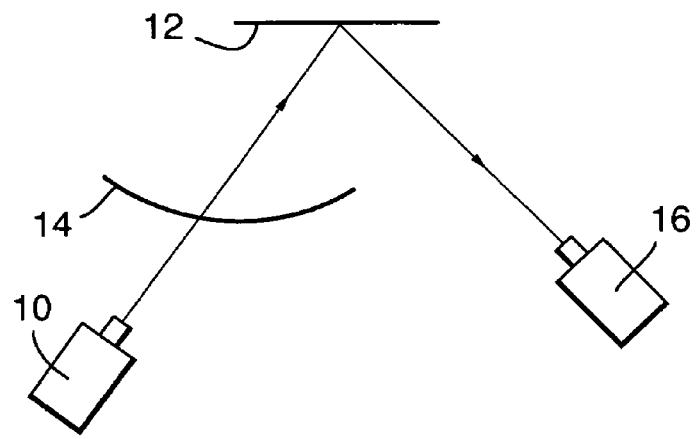
Figure 4:
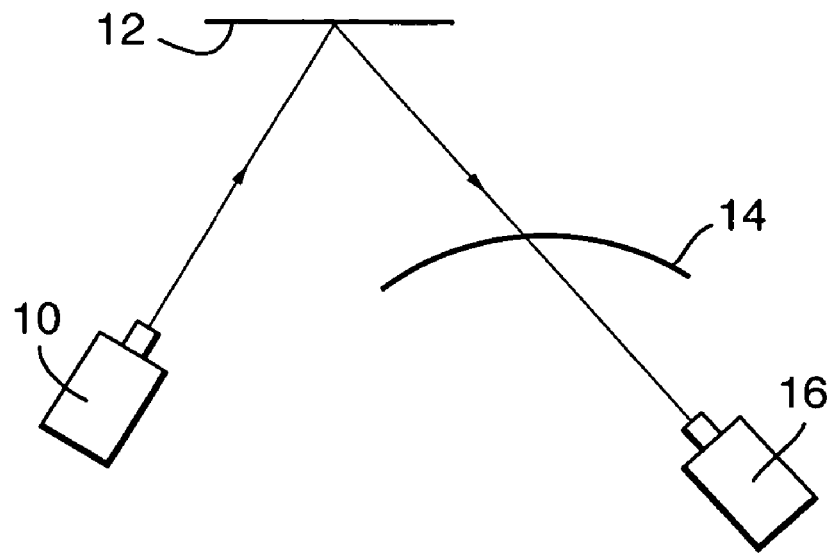

FIGS. 3 and 4 illustrate an arrangement of apparatus according to an embodiment of the invention for determining the optical quality of a glazing in transmission. In FIG. 3 a digital video projector 10 projects a sinusoidal greyscale pattern through a glazing 14 onto screen 12. A CCD camera 16 captures images of the greyscale from the screen 12. FIG. 4 illustrates an alternative arrangement where the digital video projector projects a sinusoidal greyscale pattern onto a screen 12 and CCD camera 16 captures images of the reflected greyscale pattern from the screen 12 transmitted through the glazing 14.

The processing of the captured reflected greyscale images does not form part of the present invention and is carried out by known methods in order to determine the optical quality of the glazing. The optical quality of a glazing can include its shape, curvature, rate of change of curvature, surface angle or reflected distortion. What is the concern of the present invention is the generation of the greyscale pattern. The digital video projector that generates the greyscale pattern preferably uses Digital Light Processing (DLP™) with a digital micromirror device (DMD), technology developed by Texas Instruments Inc. The DMD is a digital light switch integrated circuit having an upper surface that comprises an array of hundreds of thousands of micromirrors, each of which is responsible for directing a single pixel to the screen 12 (as in FIG. 1) or directly onto the glazing 14 (as in FIG. 2).

Figure 5:
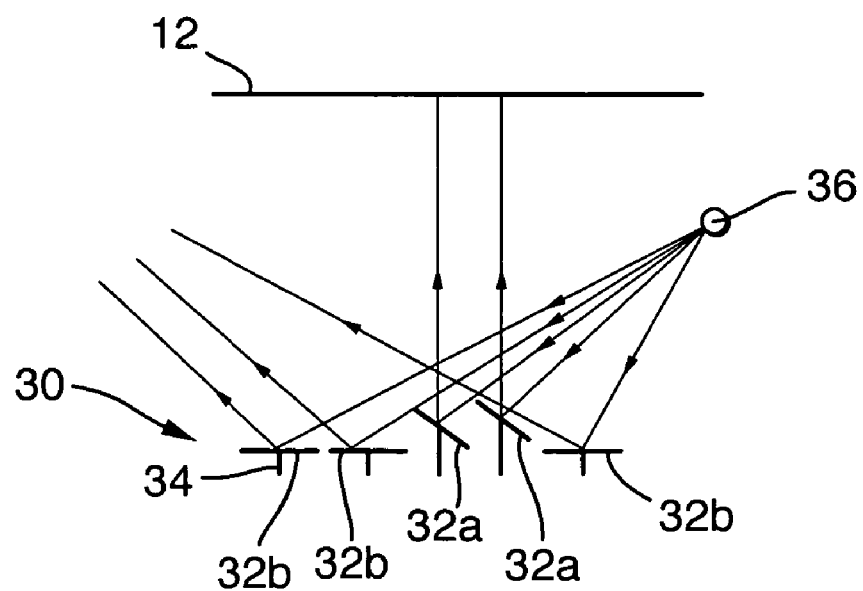
FIG. 5 is a schematic view of part of a digital mirror device (DMD)

Referring to FIG. 5, DMD 30 is used in conjunction with a light source 36 and its micromirrors 32 can reflect an all digital image onto a surface. Only a small number of micromirrors are shown to illustrate the operation of a DMD which includes hundreds of micromirrors are shown to illustrate the operation of a DMD which includes hundreds of thousands of similar micromirrors. The DMD micromirrors 32 are mounted on tiny hinges 34 which enable them to tilt either toward a light source 36 (to an ON position—illustrated by micromirrors 32a) or away from it (to an OFF position— illustrated by mirrors 32b), corresponding to a light or dark pixel on the projection surface 12. In FIG. 5 the projection surface is shown as screen 12 in accordance with the embodiments of FIGS. 1, 3 and 4, but alternatively, it could be glazing 14 in accordance with the embodiment of FIG. 2. The micromirrors 32 can switch between the ON and OFF state thousands of times per second and the duration of the ON/OFF timing determines the level of grey as perceived by the human eye seen in the pixel on the projection surface. Current DMD's can produce up to 1024 shades of grey and so can produce a highly detailed greyscale pattern.

Lamp 36 projects light towards the DMD and a bitstreamed code corresponding to the greyscale pattern to be projected reaches the DMD which then switches each of its micromirrors ON and OFF accordingly up to several thousand times per second. The time for which a particular micromirror remains ON or OFF determines the level of grey as perceived by the human eye seen in the pixel on the projection surface (where a micromirror is switched ON more frequently than OFF it produces a lighter pixel and vice versa). Current DMD's use 1024 different pulse width modulated sequences of ON and OFF to create the perception of 1024 shades of grey to the human eye. In this way a highly detailed greyscale pattern, as perceived by the human eye, is produced.

In a particularly advantageous embodiment of the invention, the exposure time of the CCD is set to be identical to the pulse width modulation period of the output of the digital video projector and synchronised with it. Use in this way facilitates a high speed system.

The output of the projector is a combination of a series of on and off pulses transmitted over a particular period, to fool the human eye into seeing a particular shade of grey. For a single mirror, the pulse width modulation period is time taken for each set of signals to repeat. For many mirrors giving up to 1024 shades of grey, the proportion of ON and OFF time for each mirror will vary but the period of the pulse width modulation of the overall signal is set to be a value that is inherent to the projector. For example, if the projector chosen has a single colour filter wheel including each of the three colours red, blue, green, the period of the pulse width modulation of the output will be the time taken for a single revolution of the colour filter wheel. If the projector has three, single colour outputs, these outputs will be synchronised for a particular time period for that projector. This time period may correspond to the AC frequency of the electrical supply powering the projector.

If the precision required is equivalent to an 8 bit scale (or 256 shades of grey), and on the basis that the individual mirrors of the DMD in the digital video projector remain ON or OFF for a minimum of 18 μsec ($18 \times 10^{-6}$ s), then the level of precision required can be obtained after leaving the CCD to integrate the incoming light for less than 5 msec ($5 \times 10^{-3}$ s) and if the exposure time of the CCD is identical with the pulse width modulation period of the digital video projector, the result measured by the camera pixel (level of greyscale) will be repeatable. Synchronising the start of the camera exposure with the projectors pulse width modulation period is particularly advantageous because the integration of light (or electrical charge) over time in a CCD camera pixel is not perfectly uniform during the exposure time. Light is converted to electrical charge which can leak away during the exposure time. Synchronising the camera exposure to the projector modulation period makes these errors inherent in the CCD camera operation repeatable. Repeatable error can be compensated for when processing camera images. Unrepeatable error always generates noise in the glass property being measured.

Alternatively, the exposure time of the CCD may be set to be an integer multiple of the period of the pulse width modulation of the projector, and synchronised with it. This is particularly useful in situations where the CCD is viewing low levels of reflected light, or viewing light though a small lens aperture.

Timing reference signals (synchronisation signals) are communicated, for example, via optical or electrical cables, connecting the digital video projector and the LCD camera. These signals may pass through other functional devices en route, for example, a computer or other digital controller. Alternatively, timing or synchronisation signals may be generated by an external functional device and input to the CCD camera and digital video projector, either directly or via a computer or other digital controller. Some example methods of synchronisation are discussed below.

The digital video projector may be used to generate the timing or synchronisation signals. One method of doing so is to devote a portion of the mirrors to sending light to a light sensing element, such as a photodiode or other photodetector. The signal from the photodetector may be used to synchronise the CCD to the pulse width modulation of the digital video projector by use of suitable electronics, such as a phase locked loop. Alternatively, the timing signal is generated by the digital video projector and received by a computer, which also receives image data from the CCD. The computer then synchronises the image data and the digital video projector output.

Although preferably the digital video projector is used to provide the timing or synchronisation signals, unless a digital video projector with a specific timing input or output is available, modification of the projector may be necessary to generate a timing signal. The light modulation process in the digital video projector is synchronised with the rotation of a red, green and blue colour filter wheel. Signals can be accessed both from the motor powering the rotation of the filter wheel, and from the sensor used to monitor the rotation of the filter. These signals can then be used to synchronise the digital video projector and the CCD.

One method of achieving this is to retain the colour filter wheel and sensor within the projector housing, but to remove them from the light path. A signal may then be taken from one of the terminals of a motor winding (used to drive the colour filter wheel and AC coupled with two capacitors for electrical isolation), and passed via a high input impedance differential amplifier to an electronic phase-locked loop circuit. The motor contacts can be selected such that the synchronisation pulses from the phase-locked loop coincide with a point in time where the projector micromirrors are off. A pulse delay circuit may be used if the synchronisation pulses from the phase-locked loop are to coincide with a different point in the projector modulation period. In order to achieve a reliable signal, the projector may need to warm up (over a period of approximately one minute) before use.

Alternatively, the colour filter wheel may be removed from the digital video projector (giving benefits to greyscale light output) and the output of the sensor monitoring the rotation of the wheel simulated. If the colour filter wheel rotation and monitoring is not simulated, the projector will not function. This simulation leads to the generation of a timing signal that may be used to synchronise the digital video projector and the CCD.

Each of these methods can be combined with a CCD having a timing input control for exposure control. Some CCD cameras have a free-run mode with user selection of aperture times for exposure control. Such a camera can provide synchronisation signals along with or contained in the recorded image signal. These synchronisation signals can be used to synchronise the projector to the camera.

If external timing signal generation is to be used, one possibility is to synchronise the pulse width modulation of the projector with the screen refresh rate of the computer controlling the projector and CCD. The exposure time of the CCD can be also be synchronised with this refresh rate. However, it is necessary to determine all other timings, not specified by the computer and the projector, and/or to assume that these must be constant.

In an alternative embodiment, the CCD exposure time may be set to be equal to or an integer multiple of the period of the pulse width modulation of the digital video projector. Synchronisation is not required, but the period of the pulse width modulation and whether it is constant needs to be determined.

In another alternative embodiment, the CCD exposure time may be set to be long in comparison with the repetition time of the pulses in the pulse width modulation cycle of the digital video projector. This embodiment is relatively inexpensive because synchronisation is not required, however, it is not suitable for high speed systems. For example, assuming one light pulse per 5 msec ($5\times10^{-3}$ s) and 8 bit precision is required (256 shades of grey), an exposure time of around 1.3 seconds is required to resolve each "grey shade" reliably.

In a still further alternative embodiment, the CCD exposure time may be set to be much shorter than the pulse width modulation cycle of the digital video projector and the respective ON/OFF periods of the pixels can be counted from successive CCD images within each pulse width modulation cycle. This method provides excellent precision but requires a very high data rate from the CCD camera, which in turn requires costly cameras and computers and so has limited use. To obtain information to 8 bit precision (256 shades of grey) would require at least 256 frames of image to be processed.

The DLP™ with DMD technology provides the benefits of high brightness, contrast ratio and image quality. In addition, because the micromirrors are so small (10-20 μm—which is less than one fifth the width of a human hair) and closely packed, the image produced is very high quality with little pixellation.

Another advantage of a DMD is that the digital switch is very efficient resulting in less noise and flicker.

What is claimed is:

1. A glazing inspection apparatus for determining the optical quality of a glazing comprising a digital video projector for generating a greyscale pattern that is reflected off or transmitted through the glazing and captured by an image capture device for subsequent processing, wherein the image capture device has an exposure time which is set to be equal to an integer multiple of a pulse width modulation period of the digital video projector.

2. An apparatus as claimed in claim 1 wherein the digital video projector includes a digital mirror device.

3. An apparatus as claimed in claim 1 further comprising synchronising means to synchronise the image capture device and the digital greyscale pattern generator.

4. An apparatus as claimed in claim 1 wherein the image capture device is a CCD camera.

5. An apparatus as claimed in claim 1, wherein the apparatus is an automotive glazing inspection apparatus.

6. A glazing inspection method for determining the optical quality of a glazing comprising:
   digitally generating a greyscale pattern through operation of a digital video prosector;
   reflecting the greyscale pattern off the glazing or transmitting it through the glazing;
   capturing the reflected or transmitted greyscale pattern using an image capture device for subsequent processing;
   wherein the image capture device has an exposure time which is set to be equal to an integer multiple of a pulse width modulation period of the digital video projector.

7. A method as claimed in claim 6 wherein generation of the greyscale pattern and capturing of the reflected or transmitted greyscale pattern are synchronised.

8. A method as claimed in claim 7 wherein the glazing is an automotive glazing and the greyscale pattern is reflected off or transmitted through the automotive glazing.

9. A method as claimed in claim 6 wherein the glazing is an automotive glazing and the greyscale pattern is reflected off or transmitted through the automotive glazing.

* * * * *